(12) United States Patent
Tsuji et al.

(10) Patent No.: US 7,642,081 B2
(45) Date of Patent: Jan. 5, 2010

(54) LACTIC ACID BACTERIA AND THEIR CELLULAR COMPONENTS INDUCING IMMUNOREGULATORY FUNCTION, AND METHOD OF OBTAINING THE SAME

(75) Inventors: Noriko Tsuji, Tsukuba (JP); Hiromi Kimoto, Tsukuba (JP)

(73) Assignees: National Institute of Agrobiological Sciences, Ibaraki (JP); Agriculture and Food Research Organization, Ibaraki (JP)

( * ) Notice: Subject to any disclaimer, the term of this patent is extended or adjusted under 35 U.S.C. 154(b) by 281 days.

(21) Appl. No.: 10/996,463

(22) Filed: Nov. 26, 2004

(65) Prior Publication Data

US 2005/0158292 A1 Jul. 21, 2005

(30) Foreign Application Priority Data

Nov. 28, 2003 (JP) ............................. 2003-398662

(51) Int. Cl.
*C12N 1/20* (2006.01)
(52) U.S. Cl. ................... 435/252.1; 435/243; 424/93.1; 424/93.4
(58) Field of Classification Search ........................ None
See application file for complete search history.

(56) References Cited

FOREIGN PATENT DOCUMENTS

| WO | WO 01/14520 A2 | 3/2001 |
|---|---|---|
| WO | WO 02/090551 A2 | 11/2002 |
| WO | WO 2004/003235 A2 | 1/2004 |

OTHER PUBLICATIONS

Miettinen et al, "Production of Human Tumor Necrosis Factor Alpha, Interleukin-6 and Interleukin-10 is Induced by Lactic Acid Bacteria," Infection and Immunity, Dec. 1996, vol. 64, No. 12, pp. 5403-5405.*
Rigby et al, "Differential Production of IL-12 and IL-10 by Colonic Dendritic Cells (DC) in Response to Bacterial Stimuli" American Gastroenterology Association (AGA) Abstracts, Apr. 2002, vol. 122, No. 4 (Suppl 1), p. A-75.*
Stagg et al, "The dendritic cell: its role in intestinal inflammation and relationship with gut bacteria" Gut, Oct. 2003, vol. 52, No. 10, pp. 1522-1529.*
Madsen et al, "*Lactobacillus* Species Prevents Colitis in Interluekin 10 Gene-Deficient Mice" May 1999, vol. 116, No. 5, pp. 1107-1114.*
von der Weid et al, "Induction by a Lactic Acid Bacterium of a Population of CD4+ T Cells with Low Proliferative Capacity That Produce Transforming Growth Factor Beta and Interleukin-10" Clinical and Diagnostic Laboratory Immunology, Jul. 2001, vol. 8, No. 4, pp. 695-701.*
Steidler et al, "Treatment of Murine Colitis by *Lactcoccus lactis* Secreting Interleukin-10" Science, Aug. 2000, vol. 289, pp. 1352-1355.*
Stanton et al, "Market Potential for Probiotics" 2001, vol. 73 (suppl), pp. 476S-483S.*
Alander et al, "Nordic Programme on In Vitro Studies of Probiotic Strains (Nordfood P93176)" International Dairy Journal, 1998, vol. 8, No. 5-6, p. 208 (abstract).*
Powell et al, "Simultaneous conjugal transfer in *Lactococcus* to genes involved in bacteriocin production and reduced susceptibility to bacteriophages" FEMS Microbiology Letters, 1990, vol. 72, pp. 209-213.*
European Search Report mailed Apr. 28, 2005, for EP 04 10 6138.

* cited by examiner

*Primary Examiner*—Allison M Ford
(74) *Attorney, Agent, or Firm*—Antonelli, Terry, Stout & Kraus, LLP.

(57) ABSTRACT

To provide a microorganism and an ingredient thereof that contribute to prevention and treatment of immune diseases including allergy, autoimmune diseases and inflammatory bowel diseases (e.g., large-intestinal ulcer), a method of effectively selecting the microorganism, and a method of efficiently inducing immunoregulatory cells that play an important role on maintaining immunological homeostasis using the microorganism or the ingredient thereof. The present invention provides a *Lactococcus* and an ingredient thereof which induce production of IL-10 from mammalian dendritic or spleen cells, a method of obtaining the microorganism or the ingredient thereof by co-culturing a microorganism such as *Lactococcus* strains with mammalian dendritic or spleen cells to select a microbial cell having a high IL-10 production ability, a method of selecting the microorganism or the ingredient thereof by co-culturing an intestinal epithelial cell with a microorganism such as the lactic acid bacteria and selecting the cells on the basis of a caspase-1 activity and the ability of inducing the production of IL-18, and a food product or material and an animal feeding stuff or medical and pharmaceutical products which contain the lactic acid bacteria as an effective ingredient.

12 Claims, 9 Drawing Sheets

LACTIC ACID BACTERIA AND THEIR CELLULAR COMPONENTS INDUCING IMMUNOREGULATORY FUNCTION, AND METHOD OF OBTAINING THE SAME

FIELD OF THE INVENTION

The present invention relates to a microorganism strain that induces an immunoregulatory function, for example, lactic acid bacteria or an ingredient having an immunoregulatory function derived from a microorganism, and to a method of obtaining the lactic acid bacteria or their cellular components. In particular, the present invention relates to a microorganism such as *Lactococcus* or cellular components derived from such a microorganism, which induces production of Interleukin-10 from mammalian dendritic or spleen cells to impart an immunoregulatory function to the cells; a method of obtaining the microorganism or its cellular components; a method of selecting the microorganism or its cellular components; and a food product, a food material, medical and pharmaceutical products, and an animal feeding stuff, which contain the microorganism or its cellular components.

DESCRIPTION OF THE BACKGROUND

The maintenance of immunological homeostasis is one of the fundamental requirements for keeping good health. Upon considering "what is the immunological homeostasis in health", an important understanding is that environmental factors largely affect functional expression of immune-related genes, i.e., differentiation and functional maturation of immune-responsive cells.

The digestive tract, covering the area about 200 times as large as that of skin, is primary interface exposed to the external environment. Therefore, enteric bacteria and food ingredients, which are representatives of the external environment in the digestive tract, are primary quantitative and qualitative environmental factors for the living body. Since the digestive tract is always exposed to a large amount of various non-self antigens and innate immune signals, it is the forefront of the bio-defense system against the majority of external immune signals, and naturally, the majority of immune related cells in the body can be found in the intestine.

In conjunction with that fact, a biological response to the enteric environment may be reflected on a rapid increase in immune diseases, typically including such as food allergy and inflammatory bowel diseases such as large-intestinal ulcer. Interestingly, it extends to other types of allergies and autoimmune diseases such as type I diabetes, which are remarkably increasing and become social issues in late years (see Kalliomaki M. et al., Lancet, 2001; 357: 1076, Stene L C and Nafstad P, Lancet, 2001; 357: 607-8).

Here, for the maintenance of immunological homeostasis, immunoregulatory cells are important. Among cell groups responsible for the balance of immunological responses, the term "immunoregulatory cells" is a generic term for a cell group that builds up a so-called self-defense mechanism for controlling an excessive immune response. In recent years, the differentiation and functional maturation mechanisms of immunoregulatory cells has gradually being clarified. In particular, it becomes clear that such mechanisms are effectively induced in the intestine (see Tsuji N. M. et al., Immunology, 2001; 458, Int. Immunol., 2003; 103: 15: 525).

As described above, a great number of environmental factors can be found in the digestive tract, and the immunoregulatory cells are responsible for avoiding an excessive response to these external antigens. Therefore, an attention has been paid thereto in the anticipation that the analysis of induction mechanisms of immunoregulatory cells in the intestine will lead to the development of technology for prevention or treatment of immune diseases.

It has become clear that the digestive tract is in an environment suitable for tolerance induction and many lymphocytes existent in the digestive tract are in an activated state. Therefore, if immunoregulatory cells are "positively" induced in the digestive tract and activated for the maintenance of immunological homeostasis, intestinal environmental should include factors that support such a phenomenon.

It is known that the digestive tract is rich in regulatory cytokines including Interleukin-10 (IL-10) and TGF-$\beta$. Also the present inventors have already revealed that Interleukin (IL-18) is an important environmental element for the induction of intestinal regulatory T cells (see Proceedings of the 32nd Annual Meeting of the Japanese Society for Immunology, 2002:256, Tsuji N M and Nowak B *Ann NY Acad Sci* (oral tolerance) 2004: in press).

To date, the development of medicines which induce immunoregulatory cells has been under way on the assumption that a chemical substance such as dexamethasone exerts such function (see Barrat F. J. et al., JEM, 2002; 195: 603).

On the other hand, a search for a microorganism and an ingredient thereof that induce immunoregulatory cells in the digestive tract has been in progress by the present inventors. In particular, if there is a microorganism which has been already used as an ingredient for food products, it can be orally administered without any problem in safety, like in the case of a chemical substance such as dexamethasone. Therefore, it can be also expected to be applied as so-called probiotics (living microorganisms that act profitably on hosts to keep them healthy) to food products for the prevention or treatment of immune diseases.

In general, among microorganisms, lactic acid bacteria are highly safe as representative probiotics and have accumulated experiences in industrial applications of food products, such as the production of fermentative food products and biodegradable resins. Besides, lactic acid bacteria have been known to exert various physiological effects based on the functionalities of lactic acid bacteria, such as the action of controlling the functions of the intestines, the action of lowering serum cholesterol levels, and the action of immunological activation when the lactic acid bacteria are taken in the body in the form of fermented milk (see Fuller, R., J. Appl. Bacteriol., 1989; 66: 365).

However, studies on microorganism and the ingredient thereof that induce immunoregulatory cells have just begun but no search and evaluation methods therefor have been established. Therefore, the microorganism and the ingredient thereof that induce immunoregulatory cells have not been found so far in lactic acid bacteria either.

SUMMARY OF THE INVENTION

The present invention has been made in consideration of the above technological background and has an object to provide a microorganism and an ingredient derived from the microorganism (*Lactococcus lactis*), in which both may contribute to prevention or treatment of immune diseases such as allergy and autoimmune diseases, a method of effectively selecting the microorganism or its cellular components, and a method of effectively inducing immunoregulatory cells that play an important role in maintenance of immunological homeostasis using the microorganism or its cellular components.

The inventors of the present invention have made extensive studies for attaining the above-mentioned object and have finally found the existence of a *Lactococcus*, which strongly supports the production of IL-10 from bone marrow-derived dendritic cells or spleen cells both from the of a mouse, among lactic acid bacteria having accumulated experiences of industrial applications related to food products, such as the production of fermentative food products and biodegradable resin.

Furthermore, generally, it has been known that germ free mice have poor immunoregulatory ability such that, for example, an immunologic tolerance state is not attained. Thus, it is strongly suggested that the microorganism and the cellular components thereof are important for the functional maturation of immunoregulatory cells. The present inventors have shown that IL-18, one of inflammatory cytokines induced by innate immune signals, are important for the generation and induction of immunoregulatory cells. IL-18 are produced as immature form and converted into active form upon innate immune signaling. As one of enzymes for converting immature form of IL-18 into active form, caspase-1 has been specifically known in the art. Surprisingly, however, it is revealed that the *Lactococcus* has an advantage of producing IL-18 from an intestinal epithelial cell independently on caspase-1. Therefore, the inventors of the present invention have found out that a substance for effectively inducing immunoregulatory cells can be effectively searched according to the activities of caspase-1 and IL-18.

The present invention has been completed on the basis of following findings.

According to a first aspect of the present invention, there is provided a *Lactococcus* or its cellular components having an immunoregulatory function through production of Interleukin-10 from mammalian dendritic cells or spleen cells.

According to a second aspect of the present invention, in the *Lactococcus* of the first aspect of the invention, the *Lactococcus* is a living (viable) bacterium or a dead (killed) bacterium.

According to a third aspect of the present invention, in the *Lactococcus* of the first or second aspect of the invention, the *Lactococcus* is *Lactococcus lactis* subsp. *cremoris* C60 strain (FERM BP-08559), and *Lactococcus lactis* subsp. *lactis* biovar diacetylactis DRC-1 strain (MAFF-400206).

According to a fourth aspect of the present invention, there is provided a method of obtaining a microorganism or its ingredient, having an immunoregulatory function, derived from the microorganism, which induces production of Interleukin-10 from mammalian dendritic cells or spleen cells, comprising: co-culturing a bacterium to be tested with the mammalian dendritic or spleen cell; and selecting a microbial strain having a high ability of inducing the production of Interleukin-10.

According to a fifth aspect of the present invention, in the method of obtaining a microorganism or its ingredient having an immunoregulatory function of the fourth aspect of the present invention, a bacterium to be tested is a *Lactococcus*.

According to a sixth aspect of the present invention, there is provided a method of selecting a microorganism or its ingredient having an immunoregulatory function, which induces production of Interleukin-10 from a mammalian dendritic or spleen cells, comprising: co-culturing a bacterium to be tested with an intestinal epithelial cell line to induce cells having a low ability of inducing caspase-1 activity and a high ability of inducing production of Interleukin-18.

According to a seventh aspect of the present invention, there is provided a food product or a food material, containing *Lactococcus* according to any one of the first to third aspects of the invention as an active ingredient.

According to an eighth aspect of the present invention, there is provided medical and pharmaceutical products, containing *Lactococcus* according to any one of the first to third aspects of the invention as an active ingredient.

According to a ninth aspect of the present invention, there is provided an animal feeding stuff, containing *Lactococcus* according to any one of the first to third aspects of the present invention as an active ingredient.

A microorganism such as a *Lactococcus* and an ingredient derived from the microorganism according to the present invention contribute to the prevention or treatment of immune diseases including allergy and autoimmune diseases such as food allergy and inflammatory bowel diseases, and contribute to maintenance of the immunological homeostasis (health maintenance) of mammals such as human beings, domestic animals, and pet animals.

In other words, the microorganism, particularly *Lactococcus*, and the ingredient derived from the microorganism of the present invention are high in safety and can be orally administered. Thus, the microorganism and the ingredient thereof are useful in that immunoregulatory cells can be efficiently induced in the body by making use of the microorganism or the cellular components thereof as an active ingredient of medical and pharmaceutical products, a food product or material, and the animal feeding stuff.

Furthermore, according to the method of the present invention, the *Lactococcus* can be obtained efficiently.

Furthermore, according to the method of the present invention, a microorganism or cellular components thereof, which efficiently induces immunoregulatory cells that play an important role in maintenance of immunological homeostasis, for example *Lactococcus*, can be selected.

DETAILED DESCRIPTION OF THE INVENTION

First of all, the first aspect of the present invention will be described in detail.

According to the first aspect of the present invention, there is provided a *Lactococcus* or cellular components derived from the *Lactococcus* having an immunoregulatory function, which induces production of Interleukin-10 from mammalian dendritic or spleen cells.

Here, mammals include experimental animals such as mice, rats, and hamsters, and also include human being and domestic animals such as cows, goats, sheep, and pigs.

The term "dendritic cells" means immunocompetent cells, which for example, can be obtained as a primary short culture of bone marrow cells from a mammal such as a mouse. Specifically, for example, bone marrow cells from a BALB/c mouse are collected and then cell groups positive for B220, CD4, CD8, and/or I-A antigen were removed, followed by culturing the cells by a conventional method in RPMI medium or DMEM medium to which cytokines such as GM-CFS (and TNF-α for human cells) were added. Then, the group of the cells (matured type) collected as suspended cells can be used. In addition, the dendritic cells suitable for the present invention can be obtained by the addition of cytokine such as Interleukin-4 (IL-4), TNF-α, or GM-CFS to monocytes from the peripheral blood.

Here, for example, the cultivation period is 8 or more days, preferably 8 to 15 days for the use of RPMI medium added with GM-CFS. If it is shorter than 8 days, there is a possibility of contamination of B cells or the like. If it exceeds 15 days, proliferation of the cells slows down and the cell number obtained becomes small.

On the other hand, the term "spleen cells" means cells derived from the spleen that consists of B cells, T cells and antigen-presenting cells such as dendritic cells and macrophages. Spleen cells can be obtained as, for example, primary culture cells of a mammal. Specifically, for example, spleen cells are obtained from BALB/c mice and then erythrocytes are removed. These suspended cells can be used for the following culture with RPMI or DMEM medium added with serum such as 10% fetal calf serum, and addition of Concanavalin-A.

The cultivation period may be 2 to 7 days when RPMI medium with serum such as 10% fetal calf serum is used. If it is shorter than 2 days, the function of inducing the production of IL-10 may be expressed insufficiently. If it is longer than 7 days, the function of primary culture cells may decrease.

As the dendritic or spleen cells described above, those directly obtained from a mammal or an already established cell line may be used.

The term "*Lactococcus*" or "*Lactococcus* strain" represents a micrococcus belonging to the genus *Lactococcus* and having an ability of producing L-type lactic acid. It may be a living bacterium or a dead bacterium as described in the second aspect of the present invention.

Examples of such *Lactococcus* strains of present invention according to the first aspect of the invention include *Lactococcus lactis* subsp. *lactis*, *Lactococcus lactis* subsp. *cremoris*, *Lactococcus lactis* subsp. *lactis* biovar diacetylactis, and *Lactococcus lactis* subsp. *hordniae*.

Examples of *Lactococcus lactis* subsp. *lactis* include: 527 strain (which is deposited in National Institute of Advanced Industrial Science and Technology AIST, International Patent Organism Depositary, Tsukuba Central 6, 1-1-1 Higashi, Tsukuba, Ibaraki, Japan, with an accession number of FERM P-18216); 712 strain (which is deposited in National Institute of Advanced Industrial Science and Technology AIST, International Patent Organism Depositary, Tsukuba Central 6, 1-1-1 Higashi, Tsukuba, Ibaraki, Japan, with an accession number of FERM P-15235); G53 and G50 strains (which are deposited in National Institute of Advanced Industrial Science and Technology AIST, International Patent Organism Depositary, Tsukuba Central 6, 1-1-1 Higashi, Tsukuba, Ibaraki, Japan, with an accession number of FERM P-18415); and H45 strain. Examples of *Lactococcus lactis* subsp. *cremoris* include C60 strain, HP strain, and ML strain. Examples of *Lactococcus lactis* subsp. *lactis* biovar diacetylactis include: N7 strain (which is deposited in National Institute of Advanced Industrial Science and Technology AIST, International Patent Organism Depositary, Tsukuba Central 6, 1-1-1 Higashi, Tsukuba, Ibaraki, Japan, with an accession number of FERM P-18217); 8W strain (which is deposited in National Institute of Advanced Industrial Science and Technology AIST, International Patent Organism Depositary, Tsukuba Central 6, 1-1-1 Higashi, Tsukuba, Ibaraki, Japan, with an accession number of FERM P-14165); and DRC-1 strain. Such *Lactococcus* strains are available from National Agriculture and Bio-oriented Research Organization, National Institute of Livestock and Grassland Science (Tsukuba, Ibaraki) and RIKEN (Wako, Saitama).

Of those examples of *Lactococcus* strains, *Lactococcus lactis* subsp. *lactis* biovar diacetylactis DRC-1 strain and *Lactococcus lactis* subsp. *cremoris* C60 strain, which have particularly high efficiency in inducing production of IL-10, are preferable.

*Lactococcus lactis* subsp. *lactis* biovar diacetylactis DRC-1 strain is deposited in Agrobiological Sciences GeneBank of National Institute of Agrobiological Sciences, with an accession number of MAFF-400206. Further, the property thereof has been described in Powell I. B. et al. FEMS Microbiol. Lett. 1990; 72: 209.

Further, *Lactococcus lactis* subsp. *cremoris* C60 strain is deposited in National Institute of Advanced Industrial Science and Technology AIST, International Patent Organism Depositary, Tsukuba Central 6, 1-1-1 Higashi, Tsukuba, Ibaraki, Japan, with an accession number of FERM BP-08559.

Furthermore, the phrase "cellular components having an immunoregulatory function derived from *Lactococcus* of the first aspect of the present invention" means an ingredient having an immunoregulatory function and constituting a microbial cell of the *Lactococcus*. The ingredient may be of a living bacterium or a dead bacterium.

Example of the cellular components derived from *Lactococcus* of the first aspect of the present invention is polysaccharide or the like, which constitutes *Lactococcus*. The ingredient maybe one having a function of inducing the production of Interleukin-10 from mammalian dendritic or spleen cells.

Then, the cellular components according to the first aspect of the present invention can be obtained from a living or dead bacterium of *Lactococcus* using any of conventional extraction and purification methods.

Besides, the cellular components of polysaccharide like the ingredient of *Lactococcus* having the function of inducing the production of Interleukin-10 from mammalian dendritic or spleen cells may be also found in other microorganisms (e.g., algae) in addition to *Lactococcus* and the ingredients of these microorganisms can be similarly utilized.

The *Lactococcus* according to the first aspect of the invention efficiently induces the production of Interleukin-10 from the mammalian dendritic or spleen cells, and thus can be efficiently obtained by selecting cell strains according to the ability of inducing the production of Interleukin-10. That is, according to the fourth aspect of the present invention, there is provided a method of obtaining the *Lactococcus*.

In other words, according to the fourth aspect of the present invention, a method of obtaining *Lactococcus* which induces production of Interleukin-10 from mammalian dendritic or spleen cells consists of: co-culturing *Lactococcus* strains to be tested with the mammalian dendritic or spleen cell; and selecting a strain having an enhanced ability of inducing the production of Interleukin-10.

The obtaining method according to the fourth aspect of the present invention has features to co-culture strains to be tested with mammalian dendritic or spleen cells and to select a strain having a high ability to induce the production of Interleukin-10.

Here, the mammalian dendritic and spleen cells are the same as those according to the first aspect of the present invention, respectively.

The bacteria to be tested include, but is not specifically limited to, *Lactococcus* strains such as, but not particularly limited to, *Lactococcus lactis* subsp. *lactis, Lactococcus lactis* subsp. *cremoris, Lactococcus lactis* subsp. *lactis* biovar diacetylactis, and *Lactococcus lactis* subsp. *hordniae*. These microorganisms are available from National Agriculture and Bio-oriented Research Organization, National Institute of Livestock and Grassland Science (Tsukuba, Ibaraki) and RIKEN (Wako, Saitama).

These *Lactococcus* strains may be living or dead bacteria. The lactic acid bacteria are cultured under optimal condition according to the ordinary procedures of culturing lactic acid bacteria in advance, and then, in the case of dead bacteria, the bacteria is sterilized by means of heating or the like, followed by washing with physiological saline, sterilized water, or the like 1 or 2 times, preferably 2 times to be used for the object of the present invention.

The culture conditions for co-culture are not particularly limited as far as the conditions allow the cell growth. For example, RPMI medium added with serum, DMEM medium, or the like is used and the cultivation of cells is performed in the presence of 5% $CO_2$ at 37° C., for 15 to 30 hours, preferably 20 to 25 hours in the case of dendritic cells, and for 40 to 55 hours, preferably 45 to 50 hours in the case of spleen cells.

The selection of a bacterial strain having an enhanced ability of inducing the production of Interleukin-10 is carried out using a method of measuring the amount of produced IL-10. Available methods include an enzyme-linked immuno-adsorbent assay (ELISA), a method of measuring an intracellular IL-10 level with a flow cytometry after dyeing, RT-PCR, and so on. For the measurement with ELISA, an OptEIA mouse IL-10 assay kit (manufactured by PharMingen Co., Ltd.) can be used in accordance with its protocol.

According to the obtaining method of the fourth aspect of the present invention, a microorganism such as a *Lactococcus* that induces the production of Interleukin-10 from mammalian dendritic or spleen cells, or an ingredient having an immunoregulatory function derived from the microorganism can be efficiently obtained. Therefore, the obtained *Lactococcus* can be used as the *Lactococcus* of the first to third aspects of the present invention.

In accordance with each of the first to third aspects of the present invention, inducing the production of Interleukin-10 by *Lactococcus* partially depends on endogenous IL-18 but does not depend on the activity of caspase-1. Therefore, a combination of the measurements of activities of IL-18 and caspase-1 allows the selection of a microorganism such as *Lactococcus* having an ability to induce IL-10 production. According to the sixth aspect of the present invention, there is provided a selection method therefor.

That is, according to the sixth aspect of the present invention, a method of selecting a microorganism strain or its ingredient having an immunoregulatory function derived from the microorganism strain, which induces production of Interleukin-10 from a mammalian dendritic or spleen cells, consists of: co-culturing a bacterium to be tested with an intestinal epithelial cell to induce cells having a low ability of inducing caspase-1 activity and an enhanced ability of inducing Interleukin-18.

The bacteria to be tested are not particularly limited as far as the bacteria will be analyzed with respect to the presence or absence of an active ingredient for inducing the production of Interleukin-10 from mammalian dendritic or spleen cells, but include microorganisms such as *Lactococcus* and ingredients thereof. The *Lactococcus* that induces the production of Interleukin-10 from mammalian dendritic or spleen cells are as described in the first to third aspects of the invention.

The intestinal epithelial cell is not particularly limited as far as it is derived from a mammal. In addition, it may be any of epithelial cells like Caco-2, an intestinal epithelial cell line derived from human tumor cells, and other established cell line such as HT-29. For instance, in the case of using Caco-2 cells, the cells are pre-cultured by the conventional method and then subjected to co-culture. That is, the cells are treated in RPMI medium containing trypsin/EDTA at 30 to 40° C. for 5 to 15 minutes to produce suspended cells and then suspended in RPMI medium containing FCS, followed by culturing for 10 to 14 days. Subsequently, the resultant co-cultured with the microbial cells that have been suspended in the RPMI medium containing FCS can be used.

In the selection method according to the sixth aspect of the present invention, for example, the microorganism such as the *Lactococcus* as described in any one of the first to third aspects of the invention is co-cultured with the intestinal epithelial cells. In this case, the culture conditions are not particularly limited as far as the conditions allow the growth of the intestinal epithelial cells. For example, in the case of Caco-2 cells, it may be cultured in RPMI medium containing FCS, DMEM medium, or the like in the presence of 5% $CO_2$ at 30 to 40° C. for 15 to 30 hours, preferably 20 to 25 hours.

In the selection method according to the sixth aspect of the present invention, after the above co-culture, cells having a low ability of inducing the activity of caspase-1 and an enhanced ability of inducing the production of Interleukin-18 are induced. That is, both the ability of inducing caspase-1 and the ability of inducing the production of Interleukin-18 are determined and the cells being low in ability of inducing the former and high in ability of inducing the latter are induced.

For determining the ability of inducing the activity of caspase-1, a fluorescent-labeled oligopeptide (e.g., a fluorescent-labeled oligopeptide, which is prepared by adding an acetyl group to the 5'-end of an amino acid sequence described in SEQ ID NO:1 of the sequence listing and fluorescent-labeling the 3'-end of the amino acid with MCA (caspase-1 activity assay reagent, manufactured by Peptide Institute, Inc.)) and a fluoro-spectrophotometer can be used.

The cells were precipitated by centrifugation and then dissolved in a buffer added with a surfactant. Then, the activity of caspase-1 in the resulting solution was determined using a fluorescent-labeled oligopeptide (oligopeptide, which is prepared by adding an acetyl group to the 5'-end of an amino acid sequence described in SEQ ID NO:1 of the sequence listing and fluorescent-labeling the 3'-end of the amino acid with MCA, (caspase-1activity assay reagent, manufactured by Peptide Institute, Inc.) and a fluoro-spectrophotometer.

For determining the ability of inducing the production of Interleukin-18, an enzyme-linked immuno-adsorbent assay (ELISA) may be used. If the measurement is carried out using ELISA, an IL-18 assay kit (manufactured by MBL Co., Ltd.) may be used in accordance with its protocol.

Consequently, a microorganism strain or a cellular component thereof, which has a low ability of inducing the activity of caspase-1 and an enhanced ability of inducing the production of Interleukin-18, can be selected. The selected microorganism strain or the ingredient has a function of inducing the production of Interleukin-10 from mammalian dendritic or spleen cells by the bacterium to be tested.

The *Lactococcus* is as described in the first aspect of the present invention.

The microorganism strain or the ingredient thereof thus selected shows the enhanced activity of another IL-18 inductive reagent (Lipopolysaccharide (LPS) or the like) even though the ability of inducing the activity of caspase-1 is low.

The specific relationship between endogenous IL-18 and IL-10 is unclear. However, when the inventors of the present invention carried out co-culture of dendritic cells derived from an IL-18 deficient mouse with the *Lactococcus* strains, a substantial reduction in amount of IL-10 produced was observed, suggesting the presence of any regulatory relationship between them.

Consequently, according to the sixth aspect of the invention, it is possible to select a microorganism or a cellular component thereof, that is capable of efficiently inducing immunoregulatory cells, i.e., inducing the production of IL-10.

On the other hand, the *Lactococcus* according to any one of the first to third aspects of the present invention is one of the lactic acid bacteria. Therefore, it can be orally administered as a food product or a pharmaceutical product, so that it is useful as probiotics exerting an immunoregulatory function in the digestive tract. Therefore, according to the seventh, eighth and ninth aspects of the present invention, there are provided a food product, a food material, medical and/or pharmaceutical products, and an animal feeding stuff.

Furthermore, the *Lactococcus* as described in any one of the first to third aspects of the present invention may be applied to medicines by making use of its characteristics that it can be orally administered and it can be used as probiotics exerting an immunoregulatory function in the digestive tract. Thus, as for the eighth aspect of the present invention, there are provided a medical and pharmaceutical product.

That is, the food product or the food material according to the seventh aspect of the present invention, the medical and/or the pharmaceutical products according to the eighth aspect of the present invention, and the animal feeding stuff according to the ninth aspect of the present invention containing *Lactococcus* as described in any one of the first to third aspects of the invention as an effective ingredient.

In the food product or food material according to the seventh aspect of the present invention, a sufficient effect can be attained in human beings by the administration of *Lactococcus* in amounts of about 0.5 to 1 mg/day per kg of body weight on the microbial cell basis. The amount of the above microbial cells may be taken once or several times a day.

In the medical and/or the pharmaceutical products according to the eighth aspect of the present invention, a sufficient effect can be attained in human beings by the administration of *Lactococcus* in amounts of about 0.5 to 2 mg/day per kg of body weight on the microbial cell basis. The amount of the above microbial cells may be administered once or several times a day.

The species and ages of animals used as targets of the animal feeding stuff according to the ninth aspect of the present invention are not particularly limited and any of animals including domestic animals such as cows, sheep, goats, and horses, and an experimental animal such as mice maybe used. A sufficient effect can be attained by a *Lactococcus* content of about 0.5 to 1 mg/day per kg of body weight on the microbial cell basis. The amount of the above microbial cells may be fed once or several times a day.

The production method for the food product or the food material according to the seventh aspect of the present invention, the production method for the medical and/or the pharmaceutical products according to the eighth aspect of the present invention, and the production method for the animal feeding stuff according to the ninth aspect of the present invention are not particularly limited, respectively. In addition, the form of each of the food product, food material, the medical and/or the pharmaceutical products, and the animal feeding stuff is not particularly limited. Any of the forms such as freeze-dried powder, spray-dried powder, and suspension to any liquid may be suitably selected for the food product, food material and animal feeding stuff, and used depending on an intended purpose. The *Lactococcus* strains grow well in milk, so that the bacterium can be used as a starter or the like to produce a fermentative food product or a fermentative animal feeding stuff.

Furthermore, it is also possible to apply the *Lactococcus* as described in any one of the first to third aspects of the present invention to the field of biodegradable plastics, which can be produced by polymerizing lactic acid prepared by fermentation of corn or potato.

EXAMPLES

Hereinafter, the present invention will be described in detail based on examples described below. However, the present invention is not limited to those examples.

Example 1

(Ability to Induce Production of IL-10 in Dendritic Cell)

Heat-killed microbial cells of each of various microorganisms including *Lactococcus* strains were subjected to co-culture with dendritic cells derived from the bone marrow to carry out the selection of a bacterial strain having a high ability of inducing the production of IL-10.

The microorganisms used were 16 strains in total, including: *Enterococcus* bacteria (IFO12964 strain, IFO13712 strain, and FH8 strain), *Leuconostoc* bacteria (D4 strain and D48 strain), *Lactobacillus* bacteria (JCM1132 strain), *Lactococcus* strains (*Lactococcus lactis* subsp. *lactis* (527 strain (FERM P-18216), 712 strain (FERM P-15235), G53 strain, and H45 strain), *Lactococcus lactis* subsp. *cremoris* (C60 strain (FERM BP-08559), HP strain, and ML strain), *Lactococcus lactis* subsp. *lactis* biovar diacetylactis (N7 strain (FERM P-18217), 8W strain (FERM P-14165), and DRC-1 strain (MAFF-400206)), which were stored in National Agriculture and Bio-oriented Research Organization, National Institute of Livestock and Grassland Science (Tsukuba, Ibaraki) or available from RIKEN (Wako, Saitama) or Institute for Fermentation (Osaka).

Those test microorganisms were cultured for 24 hours (overnight) in advance by a conventional procedure. The microorganism after cultivation was heat-killed at 70° C. for 30 minutes. Then, the microorganism was subjected to, as heat-killed microbial cells, to the procedures described below.

On the other hand, as a control, the following procedures were conducted using a group (Med) to which no immuno-modifier substance was added and using LPS (LPS derived from *E. coli* (manufactured by Sigma Co., Ltd.)), representative of an immunoactive microbial ingredient, instead of the heat-killed microbial cells of the microorganism.

On the other hand, dendritic cells derived from the bone marrow were obtained from a mouse as follows. At first, bone marrow cells were sampled from a BALB/c mouse and the cells positive for B220, CD4, CD8, and I-A antigens were removed from the sampled bone marrow cells, followed by cultivation in RPMI medium (which is an abbreviation for Roswell Park Memorial Institute medium) added with GM-CFS for 10 days.

The obtained dendritic cells were inoculated into a 24-well plate in a concentration of $5\times10^5$ cells/well and then cultured at 37° C. for 24 hours using RPMI medium added with serum (10% fetal calf serum, FCS, manufactured by Sigma CO., Ltd.).

Subsequently, the heat-killed microbial cells of the microorganism were washed two times with 0.85% saline and then suspended in the RPMI medium added with serum, followed by inoculating the cell into a 24-well plate in a concentration of $25\times10^6$ cells/well. Subsequently, the microbial cells were co-cultured with dendritic cells in the presence of 5% $CO_2$ at 37° C. for 24 hours.

After the completion of the co-culture, the supernatant of the culture was separated by centrifugation and then the content of IL-10 in the supernatant was determined using an enzyme-linked immuno-adsorbent assay (ELISA). The measurement of IL-10 was carried out using an OptEIA mouse IL-10 assay kit (manufactured by PharMingen Co., Ltd.) in accordance with its protocol.

Figure 1:
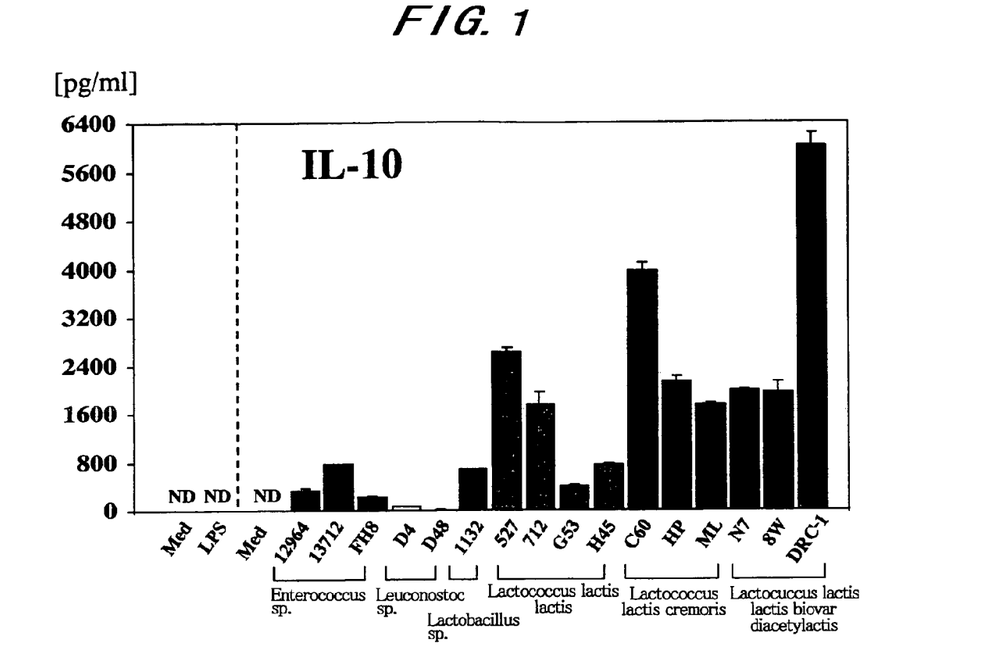
FIG. 1 is a diagram showing an amount (pg/ml) of IL-10 produced from dendritic cells derived from bone marrow stimulated with various microorganisms.

FIG. 1 shows the results of the amount of IL-10 (pg/ml) produced from the dendritic cells derived from the bone marrow with respect to each of the various microorganisms.

As shown in FIG. 1, each of 8 strains among the test microorganisms induces the production of IL-10 in large amounts and the 8 strains all correspond to *Lactococcus*. Therefore, it is revealed that each of them, *Lactococcus* strains, induces the production of IL-10 from dendritic cells derived from the bone marrow.

In particular, two strains: *Lactococcus lactis* subsp. *cremoris* C60 strain and *Lactococcus lactis* subsp. *lactis* biovar diacetylactis DRC-1 strain were found to induce IL-10 production in extremely large amounts. Therefore, it indicates that these two strains were extremely excellent in the ability of inducing the production of IL-10 from the dendritic cells derived from the bone marrow.

On the other hand, when LPS, a representative of the immunoactive microbial ingredient, was added as a control, no ability of inducing the IL-10 production was observed.

Example 2

(Ability to Induce Production of IL-10 in Spleen Cells)

Heat-killed microbial cells of each of various microorganisms including *Lactococcus* strains were subjected to co-culture with spleen cells to carry out the selection of a bacterial strain having an enhanced ability of inducing the production of IL-10.

The test microorganisms were 16 strains in total, including: *Enterococcus* bacteria (FH8 strain), *Leuconostoc* bacteria (D4 strain and D48 strain), *Lactobacillus* bacteria (JCM1132 strain and BY strain), *Lactococcus* strains (*Lactococcus lactis* subsp. *lactis* (G50 strain (FERM P-18415), 527 strain (FERM P-18216), 712 strain (FERM P-15235), G53 strain, and H45 strain), *Lactococcus lactis* subsp. *cremoris* (C60 strain (FERM BP-08559), HP strain, and ML strain), *Lactococcus lactis* subsp. *lactis* biovar diacetylactis (N7 strain (FERM P-18217), 8W strain (FERM P-14165), and DRC-1 strain (MAFF-400206)), which were stored in National Agriculture and Bio-oriented Research Organization, National Institute of Livestock and Grassland Science (Tsukuba, Ibaraki) or available from RIKEN (Wako, Saitama Japan). Using these strains, heat-killed microbial cells of the cultured microorganisms were prepared and subjected to the following procedures.

On the other hand, spleen cells were obtained from mice as follows. At first, spleen cells from BALB/c mice were depleted of erythrocytes, and washed with RPMI medium twice, followed by suspending in the same medium with the addition of serum (10% FCS). Then, the cells were inoculated into a 24-well plate at a concentration of $4\times10^6$ cells/well. Furthermore, Concanavalin A was added to each well so as to attain a final concentration of 2 μg/ml, followed by culturing at 37° C. for 2 days.

Next, the heat-killed microbial cells of the above microorganism were washed two times with 0.85% saline and then suspended in RPMI medium added with serum. Then, the resulting solution was inoculated into a 24-well plate in a concentration of $4\times10^7$ cells/well and then co-cultured with spleen cells in the presence of 5% $CO_2$ and at 37° C. for 48 hours.

Subsequently, as in Example 1, the amount of IL-10 produced was determined by an enzyme-linked immuno-adsorbent assay (ELISA).

Furthermore, as a control (Med), the culture was conducted and the amount of IL-10 produced was measured in the same way, except that the microorganism was not inoculated.

Figure 2:
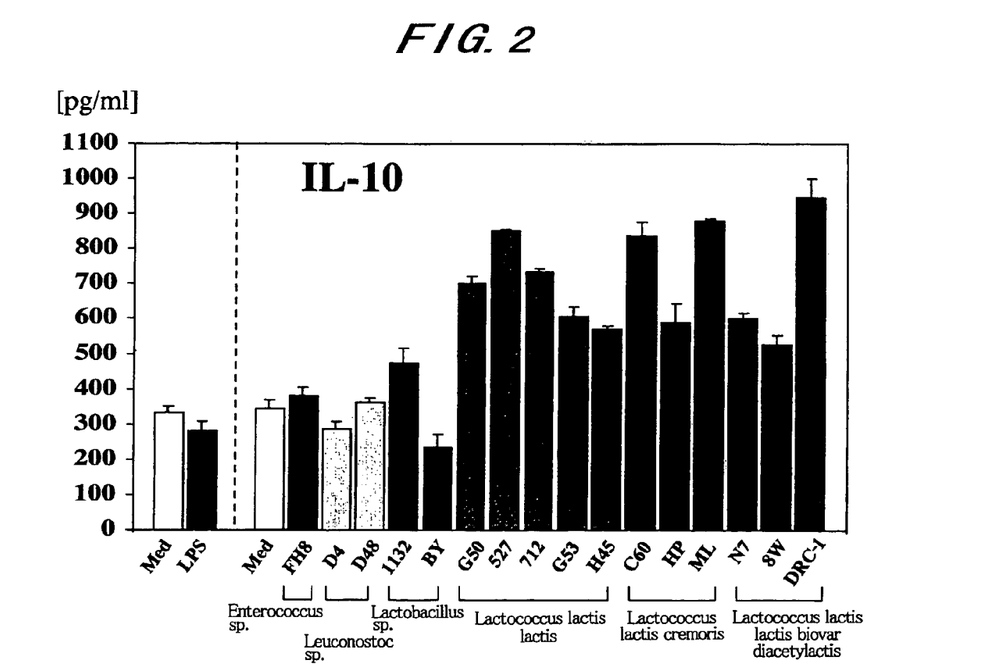
FIG. 2 is a diagram showing an amount (pg/ml) of IL-10 produced from spleen cells stimulated with various microorganisms.

FIG. 2 shows the results of the amount of IL-10 produced (pg/ml) from the spleen cells in each of the various microorganisms.

As shown in FIG. 2, each of 11 strains among the test microorganisms induces the production of IL-10 in large amounts and the 11 strains all correspond to *Lactococcus*. Therefore, it is revealed that each of them, *Lactococcus* strains, induces the production of IL-10 from spleen cells as well.

In particular, four strains: *Lactococcus lactis* subsp. *lactis* 527 strain, *Lactococcus lactis* subsp. *cremoris* C60 and ML strains, and *Lactococcus lactis* subsp. *lactis* biovar diacetylactis DRC-1 strain were found to induce IL-10 production in large amounts. Therefore, it indicates that these four strains were extremely excellent in the ability of inducing the production of IL-10 from the spleen cells.

On the other hand, in the case of adding LPS, a representative of the immunoactive microbial ingredient as a control, the ability to induce the IL-10 production was not observed.

Example 3

(Bystander Inhibition Test)

The relationship between the ability of heat-killed microbial cells of *Lactococcus* to induce the production of IL-10 from spleen cells and the bystander suppression of proliferative response of spleen cells was examined.

The *Lactococcus* strains used include *Lactococcus lactis* subsp. *cremoris* C60 strain (FERM BP-08559) and *Lactococcus lactis* subsp. *lactis* biovar diacetylactis DRC-1 strain (MAFF-400206). In addition, as a control, *Lactobacillus* bacteria (JCM1132 strain and BY strain) was used. These test microorganisms are those stored in National Agriculture and Bio-oriented Research Organization, National Institute of Livestock and Grassland Science (Tsukuba, Ibaraki) or available from RIKEN (Wako, Saitama). For each of the microorganisms, heat-killed microbial cells of the microorganism were prepared in the same way as that of Example 1.

The spleen cells prepared from BALB/c mice under the same conditions as those of Example 2 were co-cultured with the heat-killed microbial cells of the microorganism under the conditions of Example 2 (primary culture). After 48 hours, these cells were collected and the supernatant was removed by centrifugation. Subsequently, the cells were suspended in new RPMI medium (added with 10% FCS).

Next, from the spleen cells newly prepared from BALB/c mice, erythrocytes were removed and then the remainder was washed twice with RPMI medium. Subsequently, the cells were suspended in same medium added with serum (10% FCS), followed by inoculating into a 24-well plate at a concentration of $3 \times 10^6$ cells/well/ml. Furthermore, Concanavalin A was added to each well so as to attain a final concentration of 2 μg/ml (lower stage of the culture). On the other hand, a culture insert partitioned by a 0.45-μm film was loaded in each well and then spleen cells pre-cultured with the heat-killed microbial cells of the microorganism were added to the well (upper stage of the culture) in an amount of $2 \times 10^6$ spleen cells/well/500 μl, allowing co-culture at 37° C. for 2 days while only allowing a liquid factor to pass through the film (secondary culture).

After 64 hours, cells on the lower stage (newly prepared spleen cells) were collected and centrifuged to remove the supernatant, followed by suspending in 1 ml of new RPMI medium (10% FCS). A 0.1-ml aliquot of the suspension was inoculated into each well of a 96-well plate and then pulsed with 0.1 μCi of $^3$[H]-thymidine. After 16 hours, the cells were collected onto a fiber filter using a cell harvester and then immersed into a liquid scintillator to determine the uptake of radioactivity by the scintillation counter.

Furthermore, as a control (Control), the cells were cultured and subjected to the measurement of IL-10 in the same way as described above, except that no microbial ingredient was inoculated.

Figure 3:
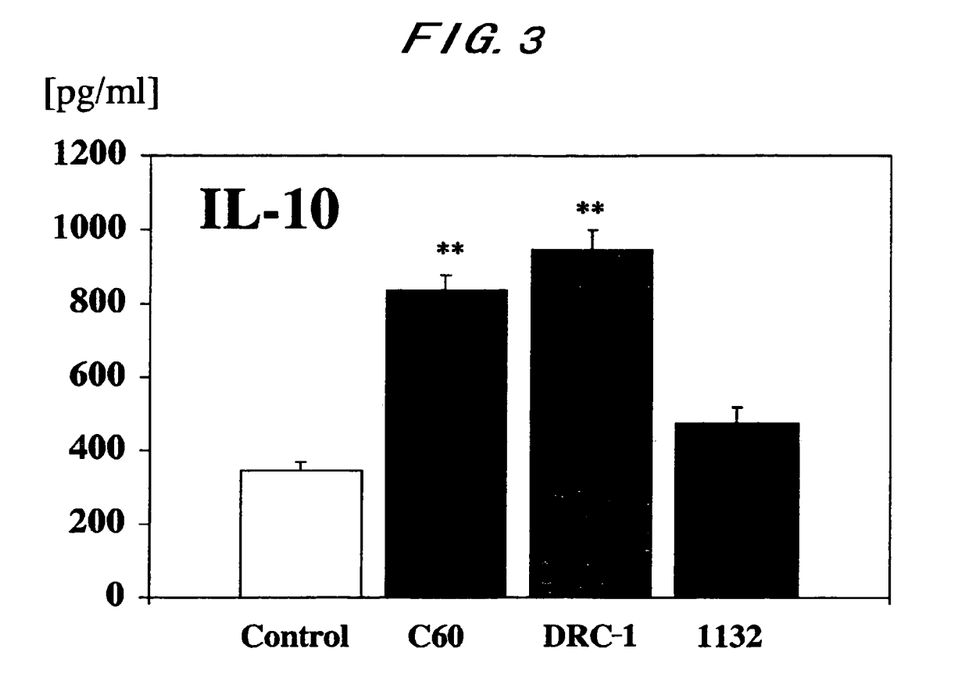
FIG. 3 is a diagram showing an amount (pg/ml) of IL-10 produced from spleen cells stimulated with various microorganisms (representative cells)

FIG. 3 shows the amount of IL-10 (pg/ml) produced from spleen cells by each of the microorganisms. In addition, FIG. 4 is a diagram showing an influence on the proliferation activity of spleen cells (c.p.m.×$10^3$) by each of the microorganisms.

Figure 4:
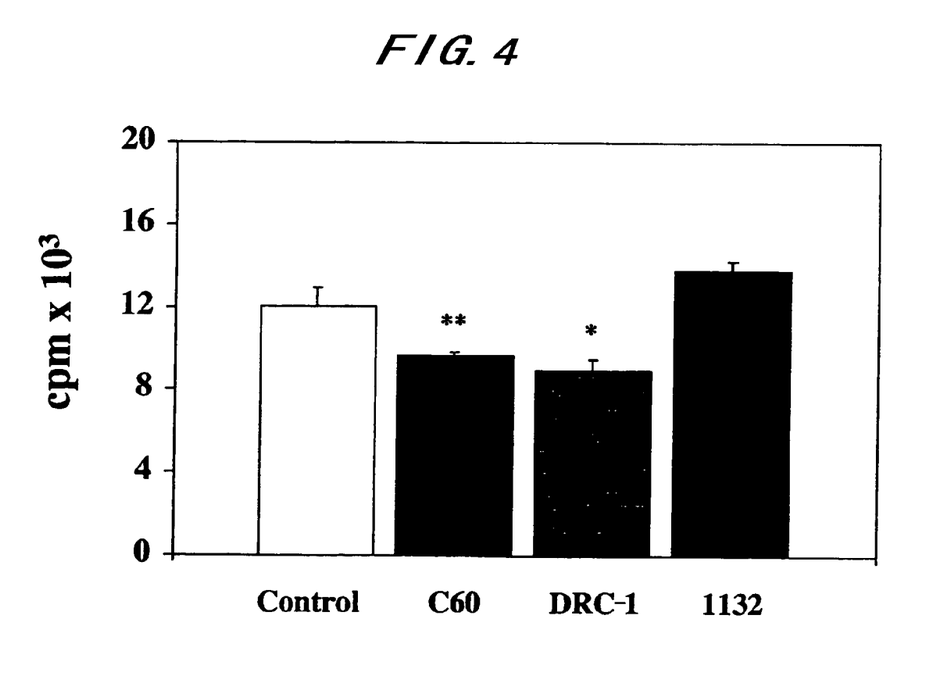
FIG. 4 is a diagram showing an influence of various microorganisms (representative cells) on a spleen cell proliferation activity (cpm×$10^3$)

In each of FIGS. 3 and 4, furthermore, denoted by ** is a significant difference ($p<0.01$) compared with "Control", and denoted by * is a significant difference ($p<0.05$) compared with "Control".

As is evident from FIG. 3 and FIG. 4, a large amount of the IL-10 produced in the supernatant of the culture medium was observed (FIG. 3) and simultaneously the proliferation activity of spleen cells on the lower stage of the secondary culture was suppressed (FIG. 4) when the *Lactococcus*, which involved the production of IL-10 in extremely large amounts in Example 2, was added in the primary culture.

The bystander inhibition test is widely used as a method of evaluating immunoregulatory cells. In this example, as described above, the activity of spleen cell proliferation was inhibited. Therefore, the heat-killed microbial cells of *Lactococcus* may induce immunoregulatory cells from the spleen cells.

Furthermore, IL-10 has strong inhibitory activity on the proliferation of cells. In this example, the cell proliferation inhibitory activity of IL-10 induced by immunoregulatory cells may play an important role in the inhibition of cell proliferation observed in this example.

Example 4

(Selection of IL-10 Production Inducible *Lactococcus* by Induction of Immunoregulatory Cells from Intestinal Epithelial Cells)

The effects of *Lactococcus* on the intestinal epithelial cells located at the forefront of the digestive tract were analyzed.

The *Lactococcus* strains used were *Lactococcus lactis* subsp. *lactis* biovar diacetylactis N7 strain (FERM P-18217), DRC-1 strain (MAFF-400206), and 8W strain (FERM P-14165). In addition, as a control, *Lactobacillus* bacterium (JCM1132 strain) was used. These test microorganisms were those stored in National Agriculture and Bio-oriented Research Organization, National Institute of Livestock and Grassland Science (Tsukuba, Ibaraki) or available from RIKEN (Wako, Saitama). For each of the microorganisms, heat-killed microbial cells of the microorganism were prepared in the same way as that of Example 1.

On the other hand, as a control, the following procedures were conducted adding, instead of the microorganism, LPS (LPS derived from *E. coli* (manufactured by Sigma Co., Ltd.)) representative of an immunoactive microbial ingredient so as to have a concentration of 1 μg/ml.

As intestinal epithelial cells, Caco-2 cells, which belong to an intestinal epithelial cell line derived from a human tumor cells, were used. That is, Caco-2 cells of the confluent culture were treated with RPMI medium containing trypsin/EDTA at 37° C. for 10 minutes to make suspended cells. Subsequently, the cells were washed twice with RPMI medium and then suspended in RPMI medium containing 10% FCS, followed by inoculating into a 24-well plate in a concentration of $4 \times 10^4$ cells/well. The supernatant was replaced with fresh RPM1 medium (10% FCS) every other day. After 10 to 14 days, the supernatant of the confluent culture ($2 \times 10^6$ cells/well) was removed all and then a suspension of microbial cells at a concentration of $1 \times 10^8$ cells/well/ml with respect to the microorganism bacterial strain was added to each well.

After 24 hours, the culture supernatant was collected by centrifugation. Then, the level of IL-18 in the supernatant was determined using the ELISA method (IL-18 assay kit, manufactured by MBL Co., Ltd.). The procedures and the conditions followed the protocol attached to the kit.

Furthermore, cells precipitated by centrifugation were dissolved in a buffer added with a surfactant. The activity of caspase-1 in the solution was determined using a fluorescent-labeled oligopeptide (e.g., a fluorescent-labeled oligopeptide, which is prepared by adding an acetyl group to the 5'-end of an amino acid sequence described in SEQ ID NO:1 of the sequence listing and fluorescent-labeling the 3'-end of the amino acid with MCA (caspase-1 activity assay reagent, manufactured by Peptide Institute, Inc.) and a fluoro-spectrophotometer.

Figure 5:
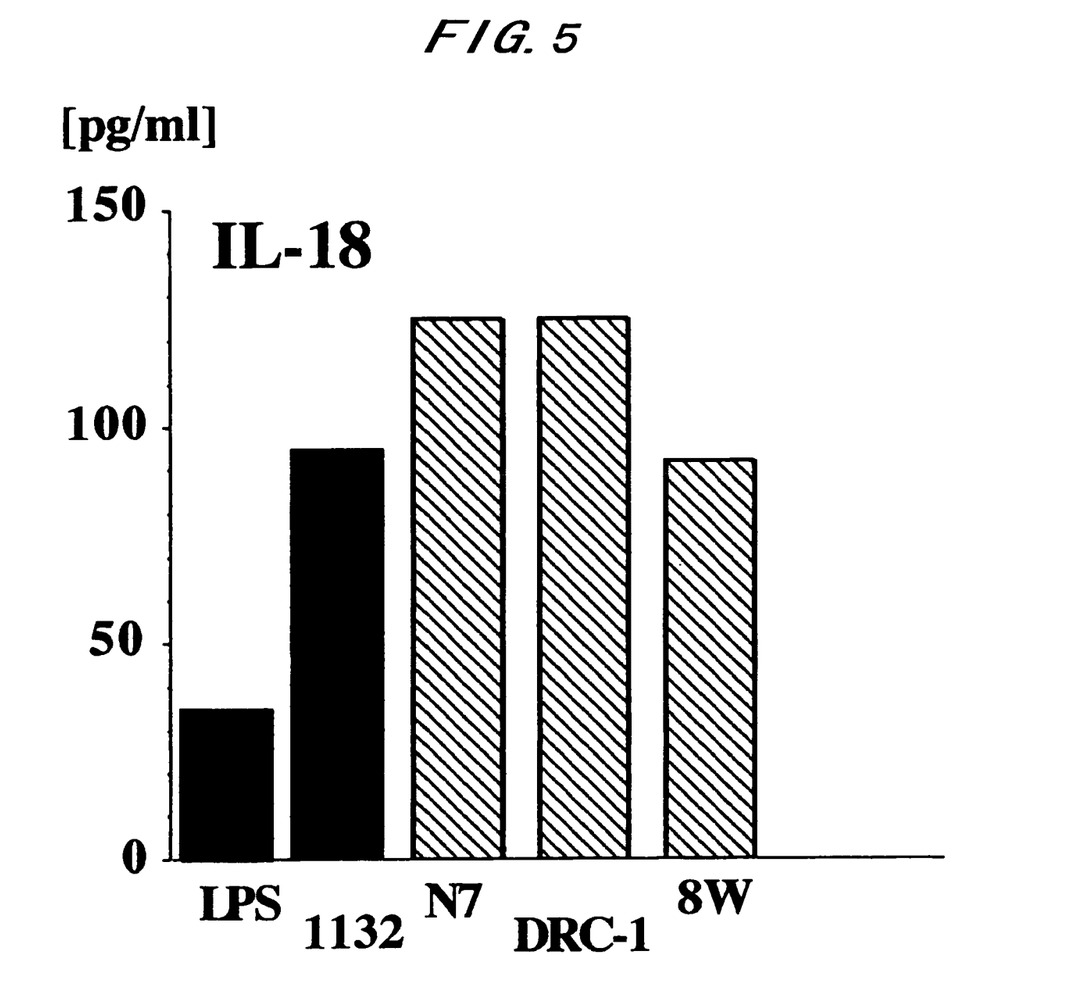
FIG. 5 is a diagram showing an amount (pg/ml) of IL-18 produced from intestinal epithelial cells stimulated with various microorganisms.
Figure 6:
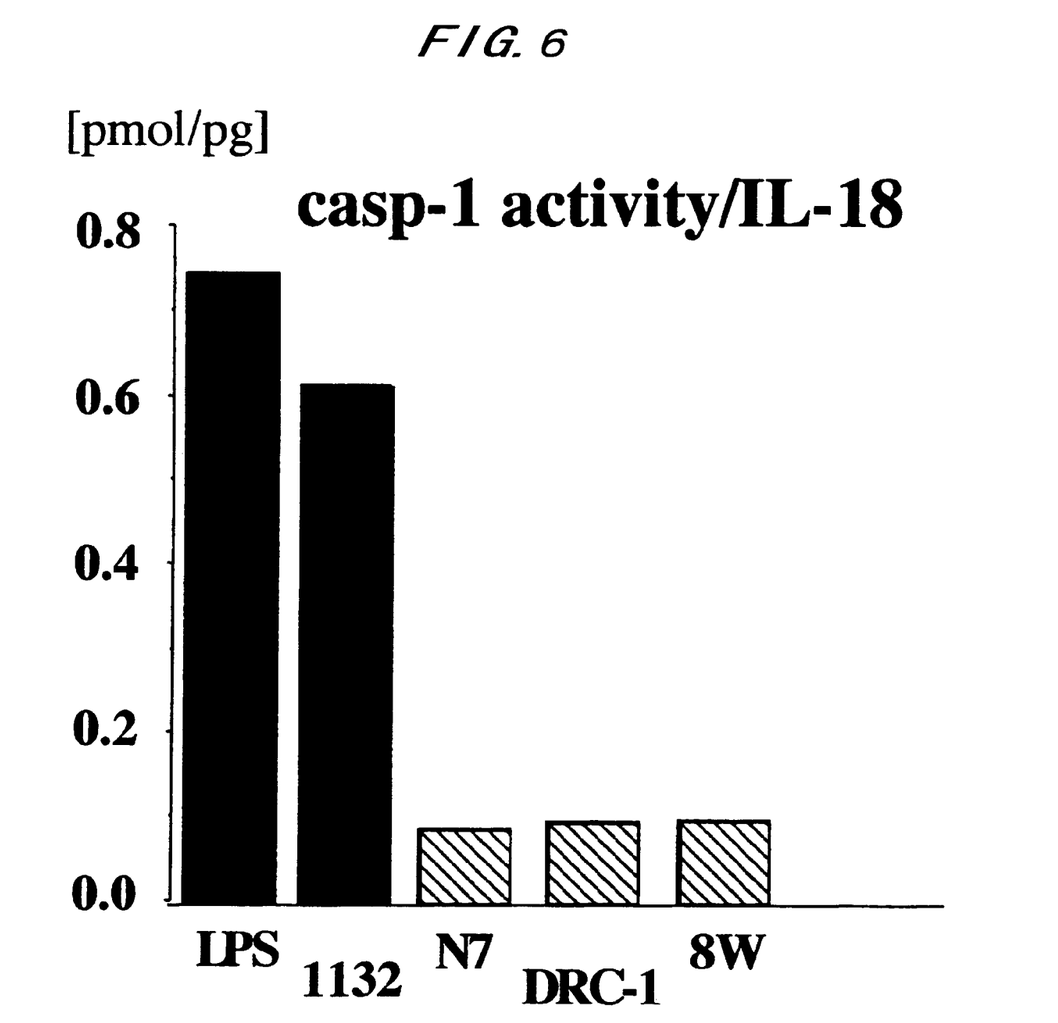
FIG. 6 is a diagram showing a caspase-1 activity (pmol) per predetermined amount of IL-18 produced from intestinal epithelial cells stimulated with various microorganisms.

FIG. 5 shows the amount of IL-18 (pg/ml) produced from intestinal epithelial cells by each microorganism. FIG. 6 shows the caspase-1 activity (pmol) per a certain amount of IL-18 produced from intestinal epithelial cells by each microorganism.

When the *Lactococcus* that showed a remarkable ability of producing IL-10 in Examples 1 to 3 was co-cultured with an intestinal epithelial cell, an enhanced ability of inducing the production of IL-18 was shown, compared with the co-culture with another microorganism or LPS (see FIG. 5). However, the activity of caspase-1 per predetermined amount of IL-18 production was kept low (see FIG. 6). In other words, one of the characteristics of the present invention has been revealed such that the production of IL-18 from an intestinal epithelial cells induced by the *Lactococcus* not depend on caspase-1.

Furthermore, an experimental system of dendritic cells has confirmed that the *Lactococcus* (*Lactococcus lactis*) induces the production of IL-18 independently of caspase-1 and has the enhanced ability to induce IL-10 production. That is, the dendritic cells derived from a caspase-1 gene deficient mouse could produce IL-18 in response to the stimulus of the *Lactococcus* (*Lactococcus lactis*).

From the above results, the inventors of the present invention have found that *Lactococcus* produces IL-18 independently of caspase-1 and induces the production of IL-10 from dendritic or spleen cells, and immunoregulatory cells can be expressed by co-culture with spleen cells.

Example 5

(In vivo Effects Upon Oral Administration of *Lactococcus*)

It was analyzed whether or not the function of inducing the IL-10 production confirmed in Examples 1 to 4 above reappears in vivo upon oral administration of heat-killed microbial cells of *Lactococcus*.

The *Lactococcus* strains used were *Lactococcus lactis* subsp. *lactis* biovar diacetylactis DRC-1 strain (MAFF-400206) and *Lactococcus lactis* subsp. *cremoris* C60 strain (FERM BP-08559). These test microorganisms were those stored in National Agriculture and Bio-oriented Research Organization, National Institute of Livestock and Grassland Science (Tsukuba, Ibaraki). Each of the microorganisms was cultured in the same way as that of Example 1 and heat-killed microbial cells of the microorganism were prepared.

The heat-killed microbial cells of the respective *Lactococcus* strains were orally administered to five NC/Nga mice of 6-8 week old once a day for ten consecutive days.

That is, the heat-killed microbial cells of the respective *Lactococcus* strains were suspended in 0.85% saline and prepared so as to have a concentration of 1 mg/ml in terms of a dry microbial weight. Each animal was subjected to intragastric administration of 200 μl (corresponding to 20 μg in terms of dry microbial weight) of the suspension each time through an oral administration sonde. After ten times of the administration, the mouse was sacrificed and spleen cells were then prepared.

The spleen cells were obtained from the mice by the following procedures. At first, erythrocytes were removed from the spleen cells of the NC/Nga mouse and then the spleen cells were washed twice with RPMI medium, followed by suspending the cells in the same medium added with serum (10% FCS). Subsequently, the spleen cells in the suspension were inoculated into a 48-well plate at a concentration of $5 \times 10^5$ cells/well. Furthermore, Concanavalin-A was added to each well so as to attain a final concentration of 2 μg/ml, followed by culturing the cells at 37° C. for 2 days.

After the completion of the cultivation, the amount of IL-10 produced was measured in the same way as that of Example 1 using the ELISA method.

Furthermore, the proliferation activity of spleen cells was determined as follows.

That is, a 0.1-ml aliquot of the culture liquid after 48 hours was inoculated into each well of a 96-well plate and 0.1 μCi of $^3$[H]-thymidine was then pulsed in the same way as that of Example 3. After 16 hours, the cells were collected on a fiber filter using a cell harvester and then immersed into a liquid scintillator, followed by determining the uptake of radioactivity using a scintillation counter.

Furthermore, as a control (saline), the cells from the group of NC/Nga mice orally administered with 0.85% saline without containing the microorganism were cultured and subjected to the measurements of IL-10 and the proliferation activity of spleen cells in the same manner.

Figure 7:
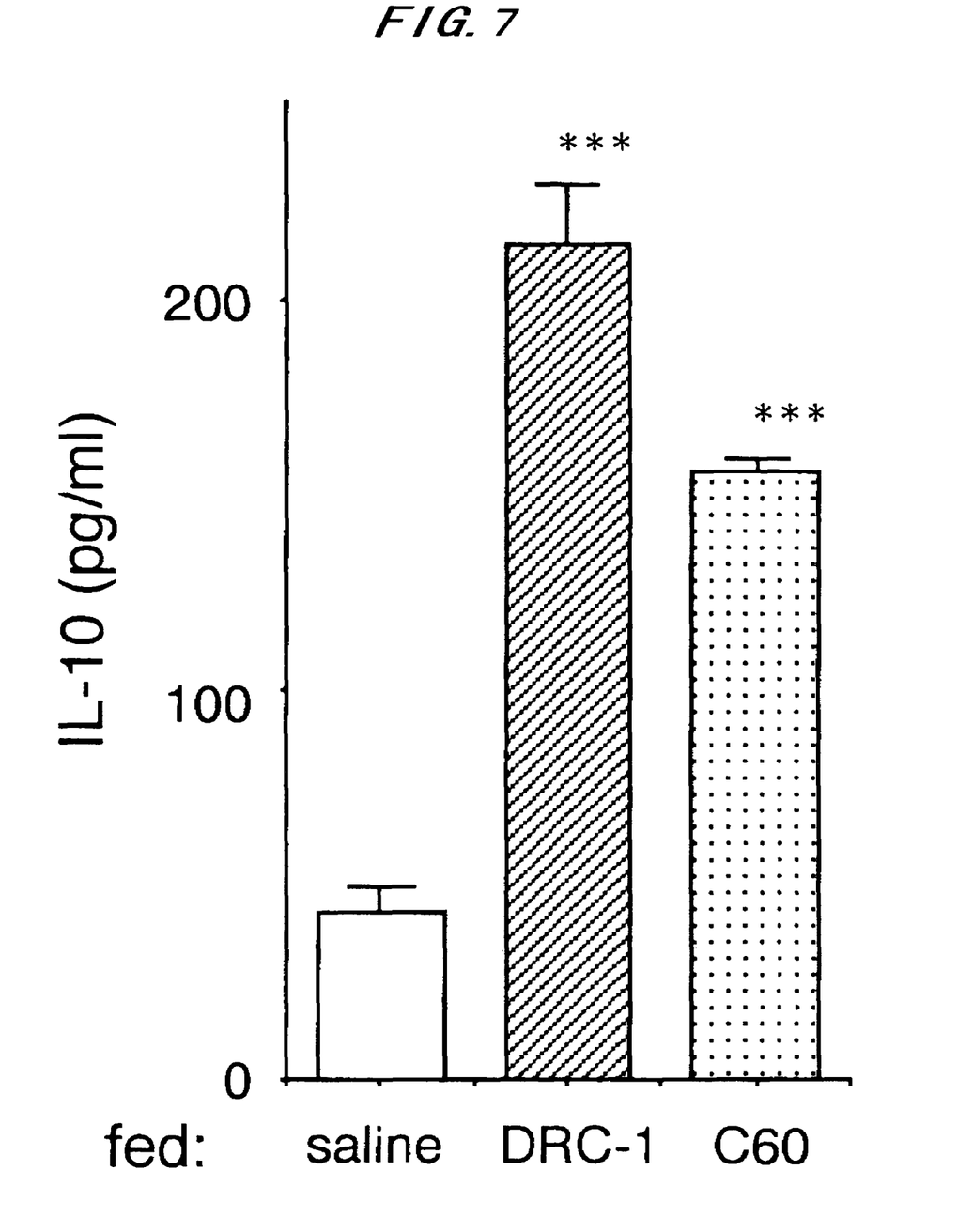
FIG. 7 is a diagram showing an amount (pg/ml) of IL-10 produced from spleen cells from mice orally administrated with various heat-killed microbial cells.
Figure 8:
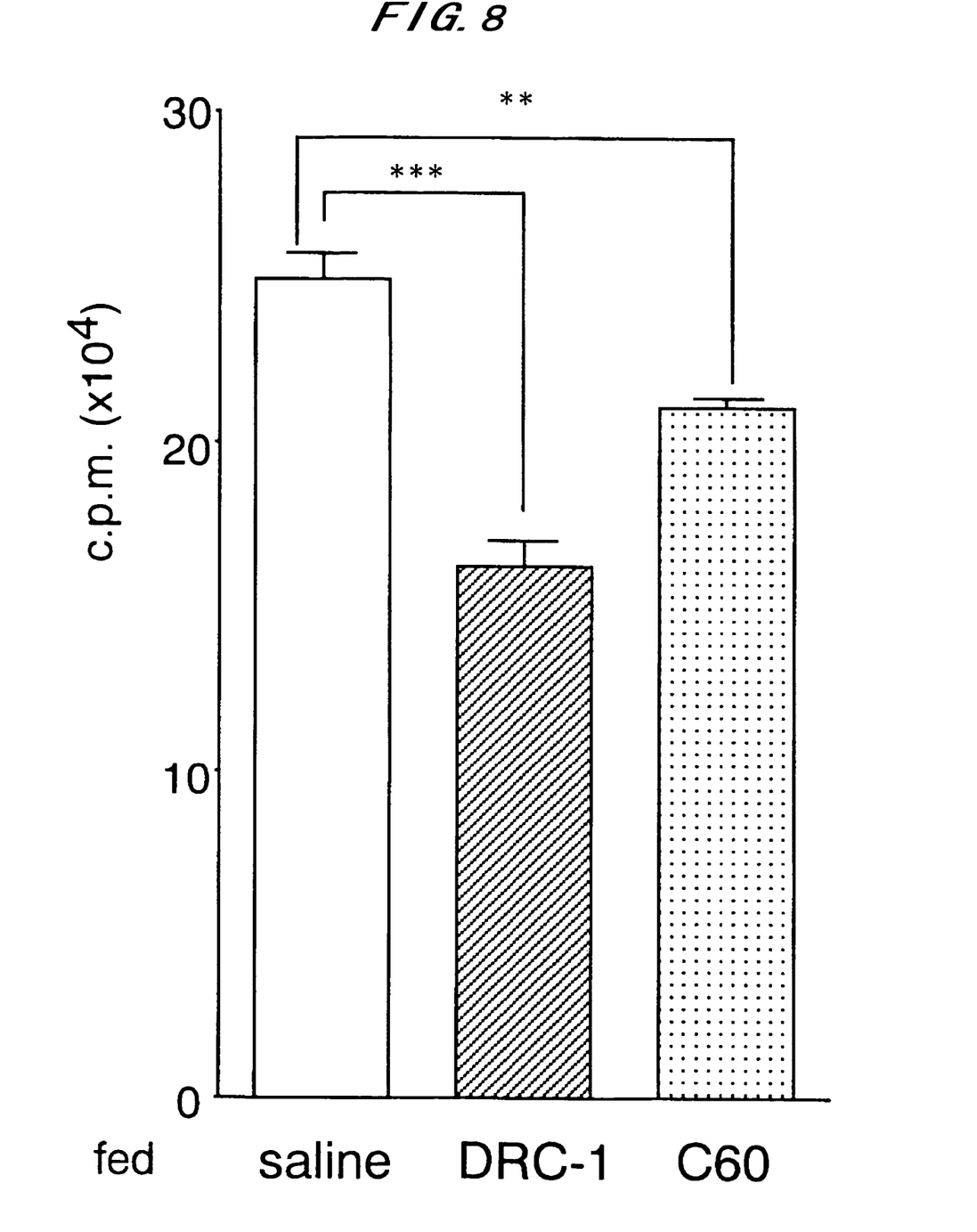
FIG. 8 is a diagram showing proliferative response of spleen cells (cpm×$10^4$) from mice orally administrated with various microorganisms.

FIG. 7 shows the amount of IL-10 (pg/ml) produced spleen cells from mice orally administered with each of the heat-killed microbial cells. FIG. 8 shows the proliferation activity of spleen cells (cpm$\times 10^4$) from mice orally administered with each of the various microorganisms. Furthermore, in FIGS. 7 and 8, denoted by * is a significant difference ($p<0.001$) compared with "saline", and denoted by ** is a significant difference ($p<0.01$) compared with "saline".

As is evident from FIG. 7, the spleen cells of the mice orally administered with heat-killed microbial cells of *Lactococcus* have been found to have an enhanced ability to produce IL-10, compared with the control. Such an enhanced IL-10 production ability may be supposedly caused as the dendritic cells, into which heat-killed microbial cells of the *Lactococcus* are taken in the digestive tract, move to the spleen or the ingredients of heat-killed microbial cells directly reach the spleen.

Furthermore, as is evident from FIG. 8, the proliferation activity of spleen cells from mice orally administered with the heat-killed microbial cells of *Lactococcus* decreases significantly with respect to the control. In consideration with the result of IL-10 production ability, such a decrease in proliferation activity of spleen cells may result from the induction of immunoregulatory cells from spleen cells during the cultivation (IL-10 is enhanced) Furthermore, the fact that T-cells in the body of a mouse obtain the properties of nonresponsiveness or suppression during the oral administration of heat-killed microbial cells for 10 days may give any influence.

Therefore, when *Lactococcus* is orally administered, it is actually confirmed in vivo that the function of inducing the production of IL-10 is retained and immunoregulatory cells are induced from spleen cells.

Example 6

(Analysis of Mechanism of a Fraction Obtained by Extraction of Lactic Acid Microbial Cells with Hot Water for Facilitating IL-10 Production)

As is evident from the above example, it is revealed that the heat-killed microbial cells of *Lactococcus* induce the production of Interleukin 10 from mammalian dendritic or spleen cells. This example is directed to confirm the presence of an ingredient having an immunoregulatory function in the lactic acid bacterium.

The *Lactococcus* strains used were *Lactococcus lactis* subsp. *lactis* biovar diacetylactis DRC-1 strain (MAFF-400206) and *Lactococcus lactis* subsp. *cremoris* C60 strain (FERM BP-08559) These test microorganisms were those stored in National Agriculture and Bio-oriented Research Organization, National Institute of Livestock and Grassland Science (Tsukuba, Ibaraki).

The fraction of *Lactococcus* strains extracted by hot water was prepared. It is considered that the majority of cellular components extracted by hot water is polysaccharides.

That is, the above *Lactococcus* was washed three times with physiological saline (or 0.85% NaCl) and the supernatant was then removed, followed by suspending in purified water of in an amount of one tenth of the remainder. Then, the mixture was heated at 100° C. for 5 hours. After heating, the residue was precipitated by centrifugation at 50,000×g for 30 minutes, followed by collecting the supernatant. Furthermore, by using a centrifugal concentration tract provided with a molecular-cut filter, the first fraction (fraction 1: Fr 1) at high molecular weight having a molecular weight of 30,000 or more and the second fraction (fraction 2: Fr 2) at a molecular weight lower than that of the first fraction were obtained. Furthermore, the extract was prepared at a 20-fold concentration factor so that the final concentration factor with a culture solution of microbial cells was about 200-fold.

The hot-water extract was added to each of the cell culture systems of dendritic cells derived from bone marrow and spleen cells, at a concentration of 10%.

A cell group derived from a BALB/c mouse after 10 days of culture was used as the dendritic cells derived from the bone marrow. The dendritic cells derived from the bone marrow were inoculated into a 96-well plate at a concentration of $1\times10^5$ cells/well and then added with Fr1, Fr2, or the heat-killed microbial cells (heat-killed DRC-1 and heat-killed C60) of the *Lactococcus* obtained in a manner similar to Example 1 in a concentration of $5\times10^6$ cells/well, followed by culturing for 24 hours. The amount of produced IL-10 in the supernatant of the culture was determined in the same way as that of Example 1.

The spleen cells used were those obtained by removing erythrocytes from the spleen cells of NC/Nga mice and washing the spleen cells twice. The spleen cells were inoculated into a 96-well plate at a concentration of $5\times10^5$ cells/well, followed by the addition of Fr1, Fr2, or the heat-killed microbial cells of the *Lactococcus* obtained in a manner similar to Example 1 at a concentration of $5\times10^6$ cells/well, followed by culturing for 96 hours. The amount of produced IL-10 in the supernatant of the culture was determined in the same way as that of Example 1.

Furthermore, as a control (medium), culture and IL-10 measurement were conducted as described above, in the absence of Fr1, Fr2, and the microbial active ingredient.

Figure 9:
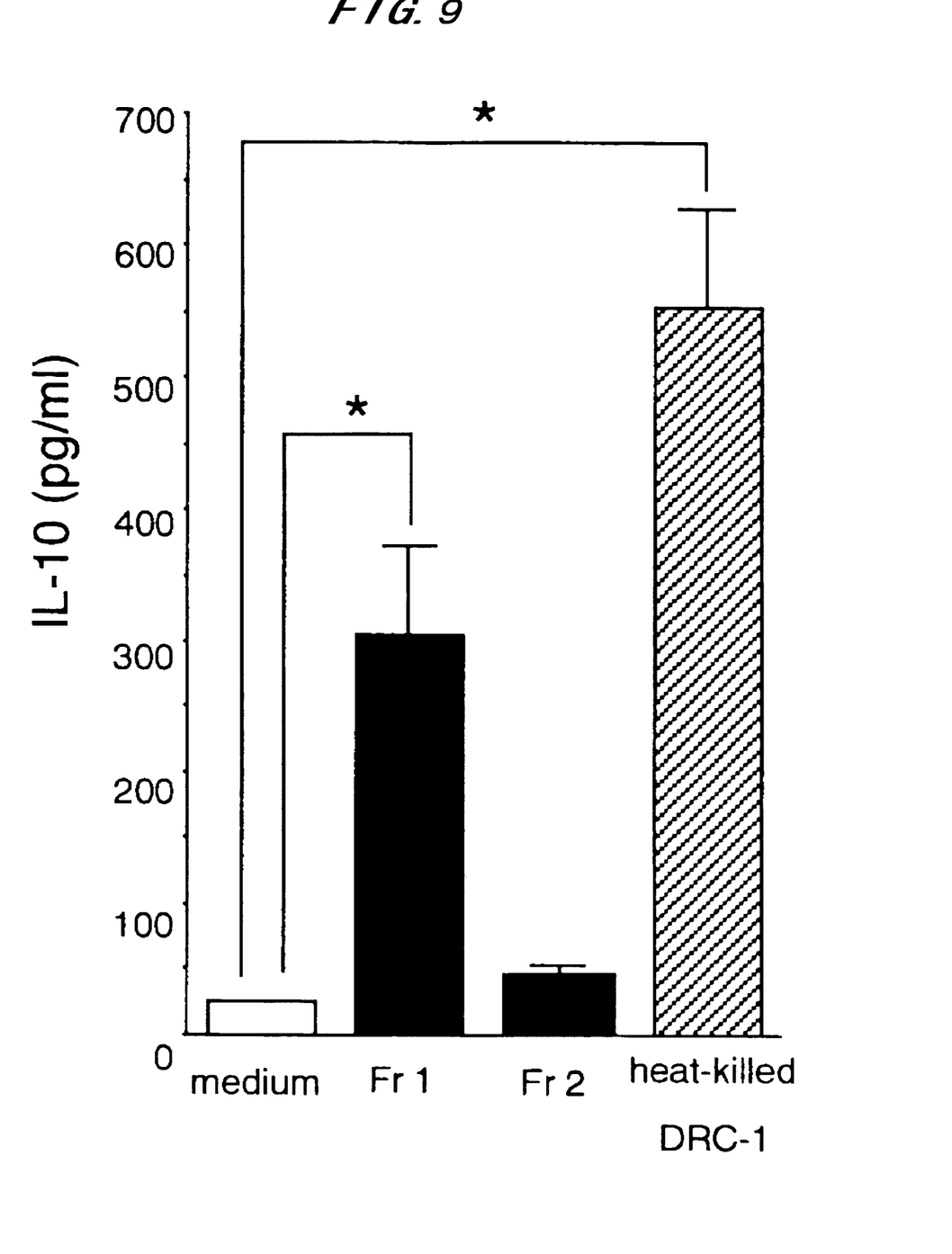
FIG. 9 is a diagram showing an amount (pg/ml) of IL-10 produced from cells derived from bone marrow in the case of using *Lactococcus lactis* subsp. *lactis* biovar diacetylactis DRC-1 strain as a stimulant.
Figure 10:
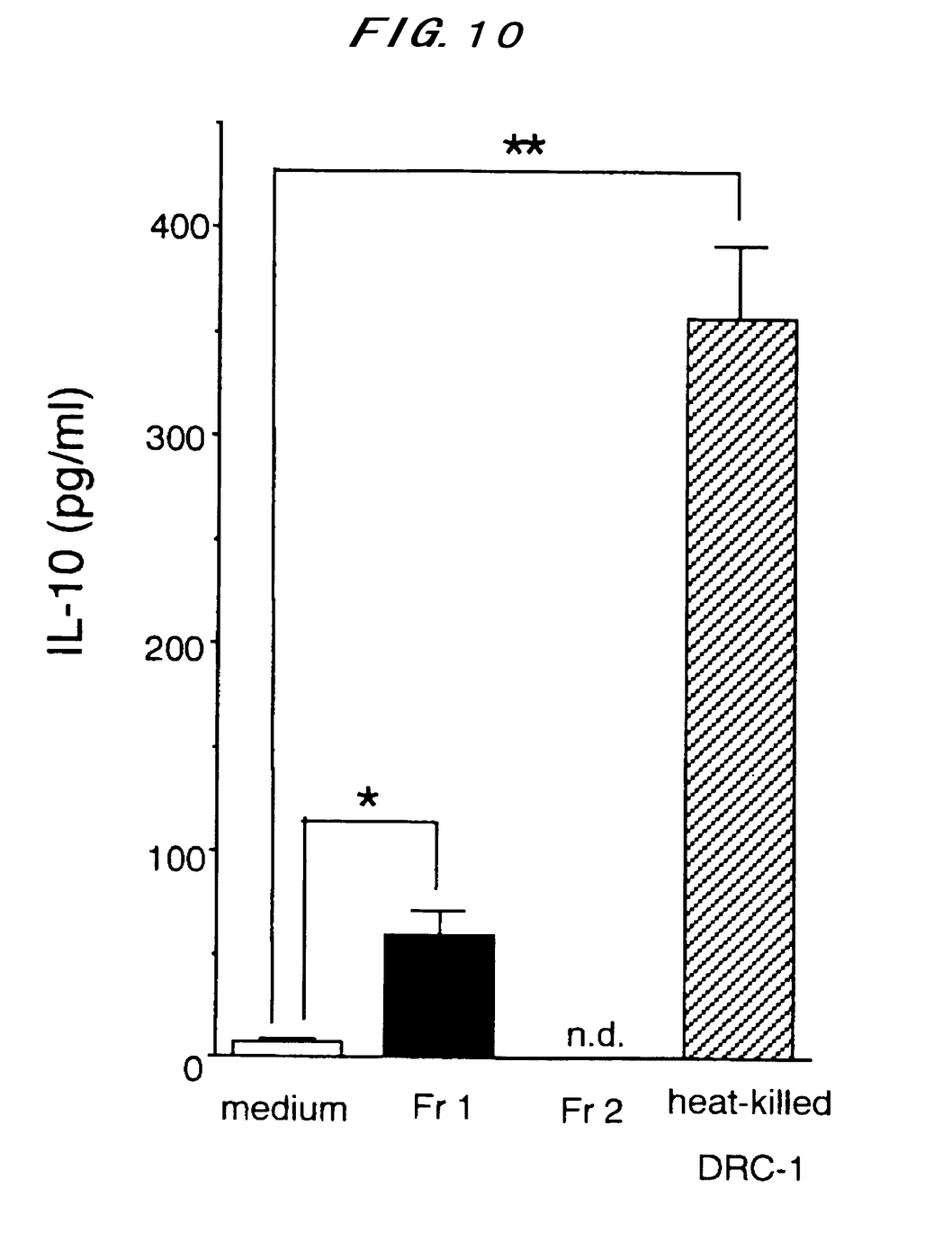
FIG. 10 is a diagram showing an amount (pg/ml) of IL-10 produced from spleen cells in the case of using *Lactococcus lactis* subsp. *lactis* biovar diacetylactis DRC-1 strain.

FIGS. 9 and 10 show the amounts (pg/ml) of IL-10 produced by the co-culture of *Lactococcus* lactis subsp. *lactis* biovar diacetylactis DRC-1 strain (MAFF-400206) with the dendritic cells derived from the bone marrow or the spleen cells, respectively.

Figure 11:
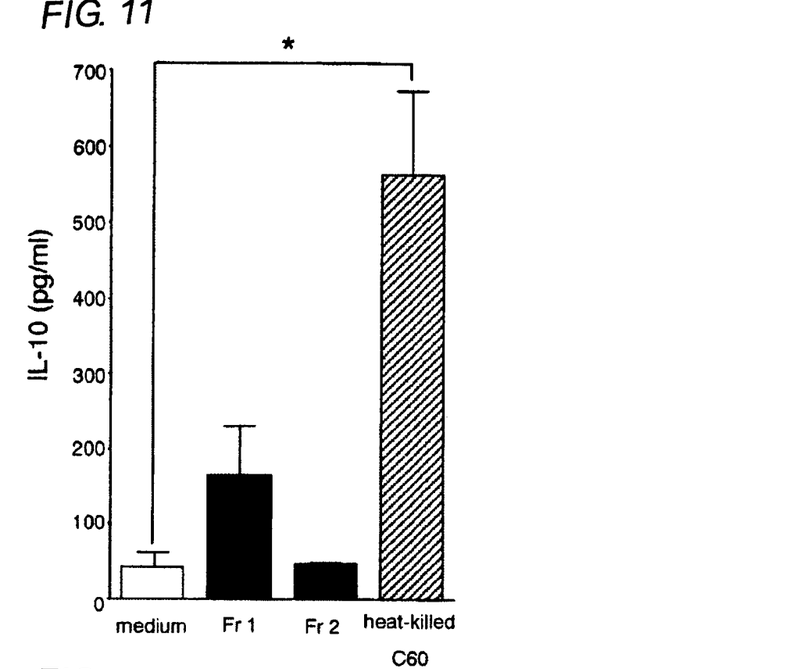
FIG. 11 is a diagram showing an amount (pg/ml) of IL-10 produced from cells derived from bone marrow in the case of using *Lactococcus lactis* subsp. *cremoris* C60 strain.
Figure 12:
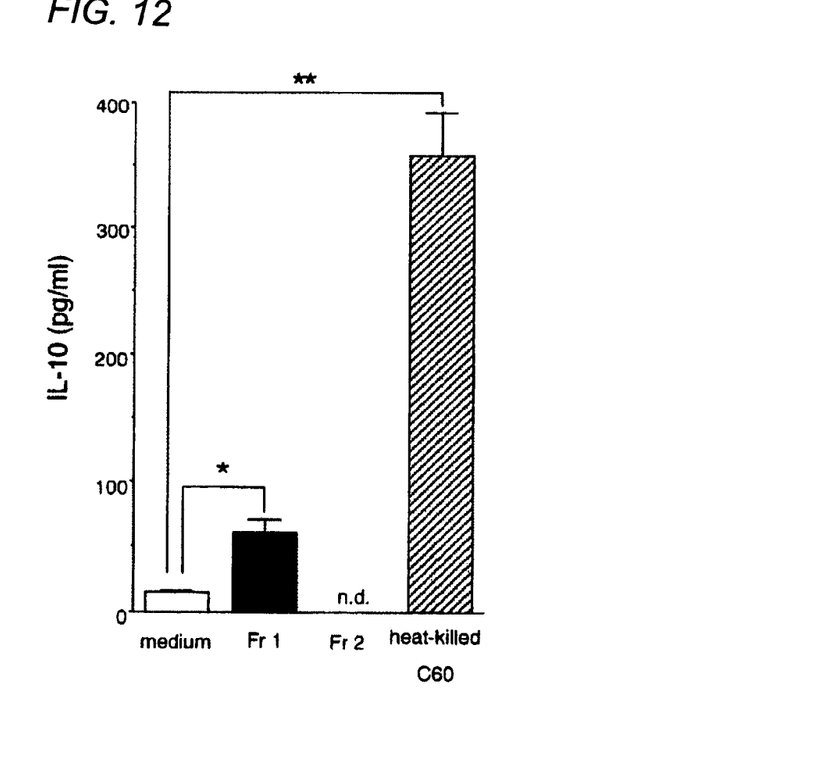
FIG. 12 is a diagram showing an amount (pg/ml) of IL-10 produced from spleen cells in the case of using *Lactococcus lactis* subsp. *cremoris* C60 strain.

In addition, FIGS. 11 and 12 show the amounts (pg/ml) of IL-10 produced by the co-culture of *Lactococcus lactis* subsp. *cremoris* C60 strain (FERM BP-08559) with the dendritic cells derived from the bone marrow or the spleen cells, respectively.

Furthermore, in FIGS. 9 to 12, denoted by ** is a significant difference ($p<0.01$) compared with "medium", and denoted by * is a significant difference ($p<0.05$) compared with "medium".

As is evident from FIGS. 9 to 12, for each cell, a significantly enhanced IL-10 production ability was observed when the fraction Fr1 was added, compared with the control. Here, it is considered that the fraction Fr1 was purified from the hot-water extract, so polysaccharide fraction was included.

Consequently, it is apparent that a high molecular weight fraction having a molecular weight of 30,000 or more derived from the *Lactococcus*, i.e., polysaccharide fraction, is an ingredient having an immunoregulatory function, i.e., a function of facilitating the induction of IL-10 production.

The *Lactococcus* and the ingredient derived therefrom in accordance with the present invention contribute to the prevention and treatment of immune disease including allergy, inflammatory bowel diseases, and autoimmune diseases, and also contribute to maintenance of the immunological homeostasis (health maintenance) of mammals such as human beings, domestic animals, or pet animals.

That is, the *Lactococcus* and the ingredient derived therefrom in accordance with the present invention are high in safety and capable of oral administration, and thus are useful in that immunoregulatory cells can be efficiently induced in the body by making use of the microorganism or the ingredient thereof as an active ingredient of a food product or material, and the animal feeding stuff.

Furthermore, according to the obtaining method of the present invention, *Lactococcus* described above can be obtained efficiently.

Furthermore, according to the selection method of the present invention, a microorganism strain or an ingredient thereof, which efficiently induces immunoregulatory cells in addition to *Lactococcus*, can be selected.

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence

```
-continued

<220> FEATURE:
<223> OTHER INFORMATION: An oligo-peptide that may be fluorescently
      labeled by adding an acetyl group to the amino end and MCA to the
      carboxyl end, useful for assaying caspase-1 activity.

<400> SEQUENCE: 1

Tyr Val Ala Asp
1
```

What is claimed is:

1. An isolated *Lactococcus* bacterium having an immunoregulatory function which induces production of interleukin-10 from mammalian dendritic or spleen cells, wherein the *Lactococcus* bacterium is *Lactococcus lactis* subsp. *cremoris* C60 (FERM BP-08559).

2. The isolated *Lactococcus* bacterium according to claim 1, wherein the *Lactococcus* bacterium is a viable bacterium.

3. The isolated *Lactococcus* bacterium according to claim 1, wherein the *Lactococcus* bacterium is a killed bacterium.

4. A food product or a food material containing the isolated *Lactococcus* bacterium according to claim 1 as an active ingredient.

5. A medical or pharmaceutical product containing the isolated *Lactococcus* bacterium according to claim 1 as an active ingredient.

6. An animal feeding stuff containing the isolated *Lactococcus* bacterium according to claim 1 as an active ingredient.

7. A food product or a food material containing the isolated *Lactococcus* bacterium according to claim 2 as an active ingredient.

8. A medical or pharmaceutical product containing the isolated *Lactococcus* bacterium according to claim 2 as an active ingredient.

9. An animal feeding stuff containing the isolated *Lactococcus* bacterium according to claim 2 as an active ingredient.

10. A food product or a food material containing the isolated *Lactococcus* bacterium according to claim 3 as an active ingredient.

11. A medical or phannaceutical product containing the isolated *Lactococcus* bacterium according to claim 3 as an active ingredient.

12. An animal feeding stuff containing the isolated *Lactococcus* bacterium according to claim 3 as an active ingredient.

* * * * *